(12) United States Patent
Tyagi et al.

(10) Patent No.: US 10,029,012 B2
(45) Date of Patent: Jul. 24, 2018

(54) PEPTIDE-MEDIATED INTRAVESICAL DELIVERY OF THERAPEUTIC AND DIAGNOSTIC AGENTS

(71) Applicant: UNIVERSITY OF PITTSBURGH—OF THE COMMONWEALTH SYSTEM OF HIGHER EDUCATION, Pittsburgh, PA (US)

(72) Inventors: Pradeep Tyagi, Pittsburgh, PA (US); Naoki Yoshimura, Pittsburgh, PA (US); Mahendra Pratap Kashyap, Pittsburgh, PA (US)

(73) Assignee: UNIVERSITY OF PITTSUBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/846,536

(22) Filed: Sep. 4, 2015

(65) Prior Publication Data

US 2016/0074521 A1  Mar. 17, 2016

Related U.S. Application Data

(60) Provisional application No. 62/046,585, filed on Sep. 5, 2014.

(51) Int. Cl.
| | |
|---|---|
| *A61K 47/42* | (2017.01) |
| *A61K 49/00* | (2006.01) |
| *A61K 31/7088* | (2006.01) |
| *A61K 47/64* | (2017.01) |
| *C12N 15/113* | (2010.01) |
| *A61K 47/68* | (2017.01) |

(52) U.S. Cl.
CPC .......... *A61K 47/42* (2013.01); *A61K 31/7088* (2013.01); *A61K 47/645* (2017.08); *A61K 49/0002* (2013.01); *A61K 47/6807* (2017.08); *C12N 15/113* (2013.01)

(58) Field of Classification Search
None
See application file for complete search history.

(56) References Cited

U.S. PATENT DOCUMENTS

| | | | | |
|---|---|---|---|---|
| 7,335,509 B2* | 2/2008 | Huang | .............. | A61K 9/1272 424/450 |
| 7,655,468 B2* | 2/2010 | Huang | .............. | A61K 9/1272 424/450 |
| 2009/0226525 A1* | 9/2009 | de los Rios | .......... | A61K 9/5184 424/489 |

FOREIGN PATENT DOCUMENTS

| | | |
|---|---|---|
| WO | WO 2002/010201 A2 | 2/2002 |
| WO | WO 2004/087931 A1 | 10/2004 |
| WO | WO 2007/069068 A2 | 6/2007 |

OTHER PUBLICATIONS

Dinauer et al. Intracellular tracking of protamine/antisense oligonucleotide nanoparticles and their inhibitory effect on HIV-1 transactivation. Journal of Controlled Release 96 (2004) 497-507.*
Cui et al. Suppression of postischemic hippocampal nerve growth factor expression by a c-fos antisense oligodeoxynucleotide. J Neurosci. Feb. 15, 1999;19(4):1335-44.*
Junghans et al. Antisense delivery using protamine-oligonucleotide particles. Nucleic Acids Res (2000) 28 (10): e45.*
UniProtKB—P04553 human sperm protamine protein.*
Human nerve growth factor (HBNF-1) mRNA, complete cds. GenBank: M57399.1 https://www.ncbi.nlm.nih.gov/nuccore/M57399.1[Dec. 11, 2017 3:40:17 PM].*
Soler et al. Urine is Necessary to Provoke Bladder Inflammation in Protamine Sulfate Induced Urothelial Injury. J Urol. Oct. 2008; 180(4):1527-31. (Year: 2008).*
Aydin et al., , "Morphological examination of the effects of defibrotide on experimentally induced bladder injury and its relation to interstitial cystitis," Urology Res, 29(4):263-271 (2001).
Barthel et al., "Gene Transfer Optimization with Lipospermine-Coated DNA," DNA and Cell Biology, 12(6):553-560 (1993).
Blietz et al., "In Vivo Studies on the Availability and Toxicity of Antisense Oligonucleotides in Bladder Cancer," in vivo, 23:13-20 (2009).
Bunnell et al., "Targeted Delivery of Antisense Oligonucleotides by Molecular Conjugates," Somatic Cell and Mol. Genet, 18(6):559-569 (1992).
Cetinel et al., "The Ameliorating Effect of Melatonin on Protamine Sulfate Induced Bladder Injury and its Relationship to Interstitial Cystitis," J. of Urology 169:1564-1568 (2003).
Chuang et al., "Intravesical Protamine Sulfate and Potassium Chloride as a Model for Bladder Hyperactivity," Urology, 61:664-670 (2003).
Dadgostar et al., "The evolving role of vascular endothelial growth factor inhibitors in the treatment of neovascular age-related macular degeneration," Eye, 22:761-767 (2008).
Degols et al., "Antiviral activity and possible mechanisms of action of oligonucleotides-poly(L-lysine) conjugates targeted to vesicular stomatitis virus mRNA and genomic RNA," Nucl. Acids Res. 17(22):9341-9350 (1989).
Elsabahy et al., "Non-Viral Nucleic Acid Delivery: Key Challenges and Future Directions," Current Drug Delivery, 8(3):235-244 (2011).
Gebhard et al., "Apolipoprotein B Antisense Inhibition—Update on Mipomersen," Curr Pharm. Design, 19:3132-3142 (2013).
Hansen et al., "Absorption of Protamine-Insulin in Diabetic Patients, I. Preparation and characterization of protamine-125 I-insulin," Horm. Metab. Res., 11:85-90 (1979).

(Continued)

*Primary Examiner* — Marcela M Cordero Garcia
*Assistant Examiner* — Jia-Hai Lee
(74) *Attorney, Agent, or Firm* — Baker Botts L.L.P.

(57) ABSTRACT

The present invention relates to compositions comprising therapeutic and/or diagnostic anionic agents together with cationic peptides and their use in methods for delivering the anionic agents to bladder cells.

12 Claims, 6 Drawing Sheets

(56) References Cited

OTHER PUBLICATIONS

Hoffmann et al., "Purification and Analysis of the Major Components of Chum Salmon Protamine Contained in Insulin Formulations Using High-Performance Liquid Chromatography," Protein Expression and Purificagtion, 1:127-133 (1990).

Jacobs et al., "Increased nerve growth factor in neurogenic overactive bladder and interstitial cystitis patients," The Canadian Journal of Urology, 17(1):4989-4994 (2010).

Junghans et al., "Phosphodiester and phosphorothioate oligonucleotide condensation and preparation of antisense nanoparticles," Biochimica et Biophysica Acta, 1544:177-188 (2001).

Kashyap et al., "Down-Regulation of Nerve Growth Factor Expression in the Bladder by Antisense Oligonucleotides as New Treatment for Overactive Bladder," J. of Urology 190:757-764 (2013).

Lavelle et al., "Bladder permeability barrier: recovery from selective injury of surface epithelial cells," Am J Physiol Renal Physiol, 283:F242-F253 (2002).

Leonetti et al., "Antiviral activity of conjugates between poly(L-lysine) and synthetic oligodeoxyribonucleotides," Gene 72:323-332 (1988).

Li et al., "Effects of Inosine on Response to In Vitro Hypoxia in Absence of Substrate on Bladder Dysfunction in Adult Rats," Urology, 73:661-664 (2009).

Lochmann et al., "Albumin-protamine—oligonucleotide nanoparticles as a new antisense delivery system. Part 1: Physicochemical characterization," Eur J Pharm and Biopharm, 59:419-429 (2005).

Lochmann et al., "Physicochemical characterization of protamine-phosphorothioate nanoparticles," J Microencapsulation, 21(6):625-641 (2004).

Martin et al., "Loss of tight junction barrier function and its role in cancer metastasis," Biochimica et Biophysica Acta, 1788:872-91 (2009).

Martin et al., "Surface-modified nanoparticles enhance transurothelial penetration and delivery of survivin siRNA in treating bladder cancer," Mol Cancer Ther., 13(1):71-81 (2014).

Nguyen et al., "Complex Formation with Plasmid DNA Increases the Cytotoxicity of Cationic Liposomes," Biol. Pharm Bull, 30(4):751-757 (2007).

Niku et al., "A New Method for Cytodestruction of Bladder Epithelium Using Protamine Sulfate and Urea," J. of Urology, 152:1025-1028 (1994).

Nogawa et al., "Intravesical administration of small interfering RNA targeting PLK-1 successfully prevents the growth of bladder cancer," J Clin Invest, 115(4):978-985 (2005).

Rodman et al., "Protamine-Reactive Natural IgM Antibodies in Human Sera, Characterization of the Epitope Demonstrates Specificity of Antigenic Recognition; Occurrence Indicates Obscurity of Origin and Function," J. Exp. Med., 167:1228-1246 (1988).

Shioyama et al., "Long-lasting breaches in the bladder epithelium lead to storage dysfunction with increase in bladder PGE2 levels in the rat," Am J Physiol Regul Integr Comp Physiol, 295:R714-R718 (2008).

Sorgi et al., "Protamine sulfate enhances lipid-mediated gene transfer," Gene Therapy 4:961-968 (1997).

Tobita et al., "Isolation and Characterization of Nuclear Basic Protein (Protamine) from Boar Spermatozoa," Biochimica et Biophysica Acta, 707:252-258 (1982).

Tyagi et al., "Intravesical Antisense Therapy for Cystitis Using TAT-Peptide Nucleic Acid Conjugates," Mol. Pharm., 3(4):398-406 (2006).

Tyagi et al., "Intravesical Liposome and Antisense Treatment for Detrusor Overactivity and Interstitial Cystitis/Painful Bladder Syndrome," ISRN Pharmacology, vol. 2014 Article ID 601653:12 pages (2014).

Tzan et al., "Effect of Protamine Sulfate on the Permeability Properties of the Mammalian Urinary Bladder," J. Membrane Biol., 133:227-242 (1993).

Tzan et al., "Mammalian urinary bladder permeability is altered by cationic proteins: modulation by divalent cations," Am J Physiol, 267(4 Pt 1):C1013-1026 (1994).

Uhlmann et al., "Studies on the Mechanism of Stabilization of Partially Phosphorothioated Oligonucleotides Against Nucleolytic Degradation," Antisense & Nucleic Acid Drug Development 7:345-350 (1997).

Wojcik et al., "Nucleotide Pyrophosphatase/Phosphodiesterase 1 is Responsible for Degradation of Antisense Phosphorothioate Oligonucleotides," Oligonucleotides, 17:134-145 (2007).

* cited by examiner

FIGURE 1A-F
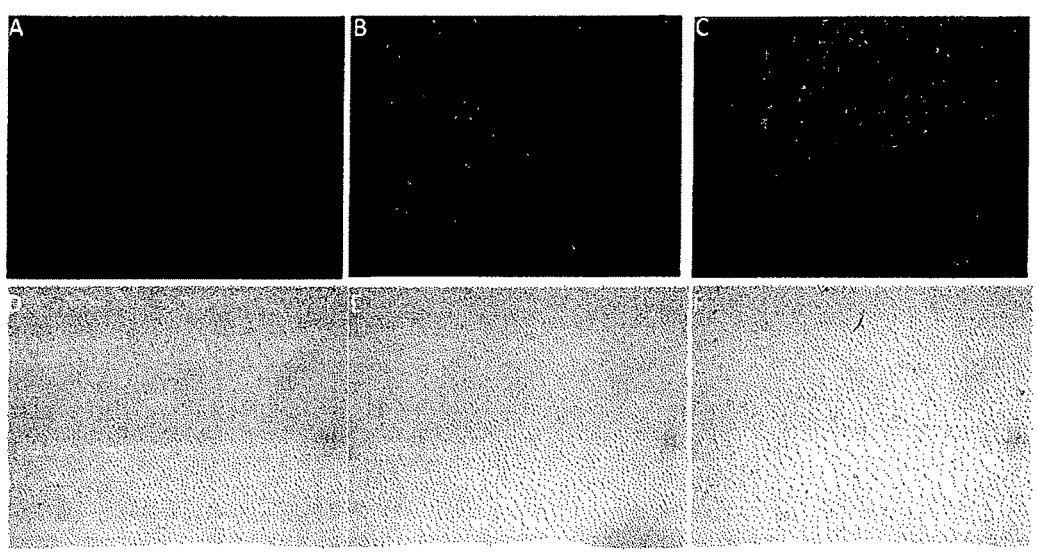

PEPTIDE-MEDIATED INTRAVESICAL DELIVERY OF THERAPEUTIC AND DIAGNOSTIC AGENTS

PRIORITY CLAIM

This application claims priority to United States Provisional Application No. 62/046,585 filed Sep. 5, 2014, the contents of which is hereby incorporated by reference in its entirety herein.

GRANT INFORMATION

This invention was made with government support under Grant No. DK088836 awarded by the National Institutes of Health. The government has certain rights in the invention.

INTRODUCTION

The present invention relates to methods and compositions for administering agents to cells in the bladder, whereby a cationic peptide or a mixture of cationic peptides is used to deliver an anionic therapeutic or diagnostic agent.

BACKGROUND OF THE INVENTION

Introduction of short strands of antisense DNA with sequences complementary to the mRNA encoding a particular protein inside the cell is being explored as a therapeutic approach[1]. The inserted antisense oligonucleotide ("ODN") binds specifically and strongly to its mRNA target through Watson-Crick base pairing and blocks gene expression either through translational inhibition or enzymatic cleavage of the mRNA target [2]. Antisense therapeutics have been under clinical investigation for more than 30 years[3] for several diseases [4].

Considering the anatomical architecture of bladder, the therapeutic principle for intravesical instillation of ODN is very appealing as it provides ease of local administration with restricted systemic side effects due to limited serum uptake of antisense ODN. However, applied research for bladder diseases has lagged behind other disciplines. Drug development of this approach has been hampered by inefficient cellular uptake of the ODN. Bladder uptake of naked ODN is generally poor, but is improved in presence of bladder cancer, when very high concentration of naked ODN [5] is instilled. It is known that tight junctions in urothelium are compromised in cancerous condition [6] and therefore the strategy of relying on concentration gradient may not work in non-cancerous diseased condition where the barrier is intact, such as in overactive bladder.

Several approaches have been tried to increase the bladder uptake of ODN without compromising the bladder barrier, but all have limitations. Cationic lipids have been used in the past to deliver ODN [7, 8], but that method requires organic solvents and expert handling for formulating the ODN and lipid together prior to use. The binding between the negatively charged DNA phosphate groups and the cationic lipid [8] or peptide carrier is achieved by ionic interaction. Traditional approaches using cationic peptides or polysaccharides [9] require covalent binding between the vector and the drug. Covalent binding to cationic peptide polylysine requires elaborate application of chemistry tools [10, 11].

The translation of basic antisense research into therapeutics is also impeded by intracellular stability of ODN and potential for "off-target" gene silencing, immunostimulation, and other side effects. Phosphorothioate-modified ODN[12] are lipophilic and have increased stability against nucleolytic degradation [13].

A significant limitation for medicine, particularly treatments given by the intravesical route (via a catheter into the bladder), is the poor permeability of the bladder to outside agents. Efficient cellular uptake of many chemical agents is still a challenge.

SUMMARY OF THE INVENTION

The present invention relates to compositions comprising therapeutic and/or diagnostic anionic agents together with cationic peptides and their use in methods for delivering the anionic agents to bladder cells. In particular non-limiting embodiments, a composition comprises an anionic drug or antisense oligonucleotide and a mixture of cationic peptides comprising protamine, and is used for intravesical drug delivery. Without being bound to any particular theory, it is believed that the cationic peptide(s) acts as a carrier through non-covalent association with the anionic agent and facilitates delivery of the agent into bladder cells.

DETAILED DESCRIPTION OF THE INVENTION

Figure 1:
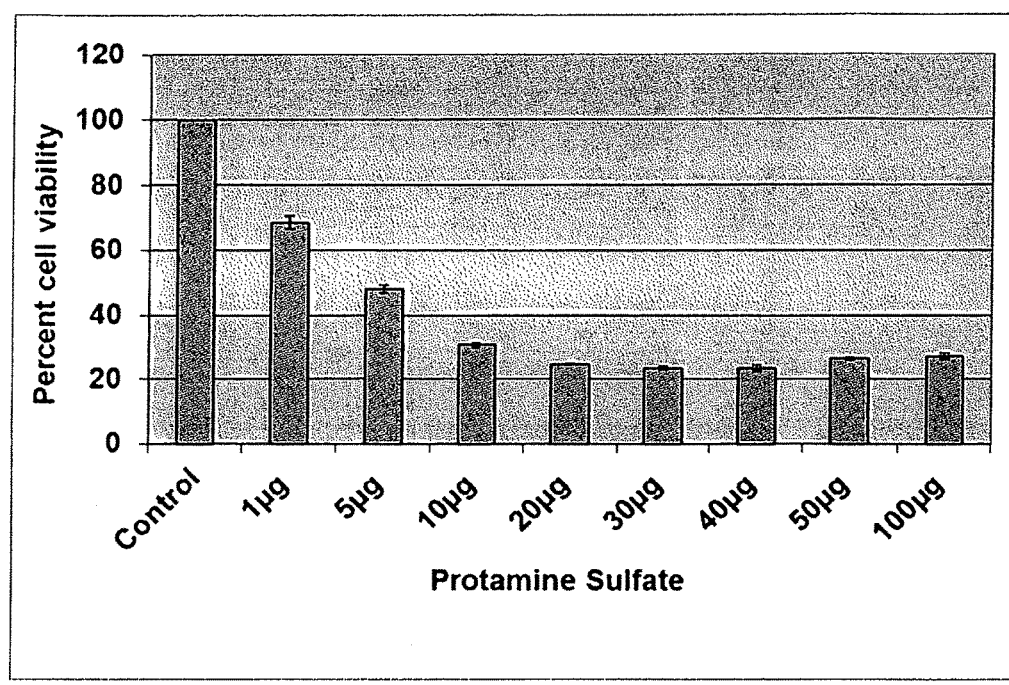
FIG. 1A-G. (A-F) Cellular uptake studies of ODN: UROtsa cells were incubated for 4 h at 37° C. with (A) naked 5'-TYE™ 563 labelled Phosphorothioate oligonucleotide (ODN), (B) 1:1 (C) 1:5 ODN/protamine particles. Cells were washed at the end of 4 h exposure to ODN mixture and the fluorescent images were captured following further incubation of treated cells for 24 hours at 37° C. The bright red fluorescence demonstrates successful uptake and retention of ODN. Respective bright field images are shown below in panels D, E and F. The amount of fluorescent oligonucleotide added to each well was always 1 μg and the protamine amount varied from 0, 1 and 5 μg in panels A, B and C, respectively. Exposure time in panel A with naked ODN was 5 sec and it was 1.2 sec in other panels at 10× magnification. (G) Effect of increasing protamine concentrations on viability of UROtsa cells is shown.

The present invention relates to methods and compositions for administering agents to cells in the bladder, whereby a cationic peptide or mixture of cationic peptides is used to deliver one or more anionic therapeutic or diagnostic agents.

A cell in the bladder may be any cell located in the bladder, including, but not limited to, a urothelial cell (which also may be referred to as a "uroepithelial cell") which may be an umbrella, intermediate, or basal cell, a muscle cell, a fibroblast, an endothelial cell or a cancerous bladder cell, for example a urothelial carcinoma cell.

A "cationic peptide" is a peptide that has a net positive charge. In certain non-limiting embodiments the peptide is at least about 15 amino acids long, or at least about 20 amino acids long, or at least about 25 amino acids long, or at least about 30 amino acids long, and/or up to about 40 amino acids long, up to about 50 amino acids long, up to about 60 amino acids long, up to about 70 amino acids long, or between about 15 and 70 amino acids long, or between about 20 and 60 amino acids long, or between about 20 and 50 amino acids long. In certain non-limiting embodiments, the cationic peptide comprises at least 30 percent or at least 50 percent positively or potentially positively charged amino acid residues selected from the group consisting of arginine, lysine, histidine, or mixtures thereof. In certain non-limiting embodiments, the cationic peptide comprises at least 30 percent or at least 50 percent arginine residues (relative to total number of amino acid residues). In certain non-limiting embodiments a cationic peptide according to the invention may comprise, alone or in combination, where the single letter code for amino acids is used:

MARYRCCRSQ SRSRYYRQRQ RSRRRRRRSC QTRRRAMRCC RPRYRPRCRR H (Homo sapiens; UniProtKB/Swiss-Prot: PO4553.2; SEQ ID NO:1);

MVRYRVRSLS ERSHEVYRQQ LHGQEQGHHG QEEQGLSPEH VEVYERTHGQ SHYRRRHCSR RRLHRIHRRQ HRSCRRRKRR SCRHRRRHRR GCR-TRKRTCR RH (Homo sapiens; UniProtKB/Swiss-Prot: PO4554.3; SEQ ID NO:2);

MRRQASLPAR RRRRVRRTRV VRRRRRVGRR RH (Oryzias latipes; NCBI Reference Sequence: NP 001098274.1; SEQ ID NO:3);

PRRRRRSSSR PIRRRRRPRAS RRRRRGGRRR R (chum salmon peak A peptide; SEQ ID NO:4; European Medicines Agency, 15 Nov. 2012, EMA/741250/2012, Assessment report for Protamine containing medicinal products, Review under Article 5(3) of Regulation (EC) No 726/2004, citing Hoffman et al., 1990);

PRRRRSSRRP VRRRRRPRVSR RRRRGGRRRR (chum salmon peak 13 peptide; SEQ ID NO:5; European Medicines Agency, 15 Nov. 2012, EMA/741250/2012, Assessment report for Protamine containing medicinal products, Review under Article 5(3) of Regulation (EC) No 726/2004, citing Hoffman et al., 1990);

PRRRRSSSRP VRRRRRPRVSR RRRRGGRRRR (chum salmon peak C peptide; SEQ ID NO:6; European Medicines Agency, 15 Nov. 2012, EMA/741250/2012, Assessment report for Protamine containing medicinal products, Review under Article 5(3) of Regulation (EC) No 726/2004, citing Hoffman et al., 1990); PRRRRASRRI RRRRRPRVSR RRRRGGRRRR (chum salmon peak D peptide; SEQ ID NO:7; European Medicines Agency, 15 Nov. 2012, EMA/741250/2012, Assessment report for Protamine containing medicinal products, Review under Article 5(3) of Regulation (EC) No 726/2004, citing Hoffman et al., 1990); or a peptide comprising the sequence $RRRX_1 X_2 RRR$ where $X_1$ or $X_2$ or both is/are G or V or A (SEQ ID NO:8).

In certain non-limiting embodiments, a single species of cationic peptide is used for delivery in the delivery formulation. In certain other non-limiting embodiments of the invention, a mixture of cationic peptides is used. In certain non-limiting embodiments of the invention, a mixture of cationic peptides commercially available as protamine sulfate is used. In a specific non-limiting embodiment the protamine sulfate may be as approved by the United States Food and Drug Administration, for example, as provided in a 10 mg/mL solution by Fresenius Kabi U.S.A. or an equivalent product.

In certain non-limiting embodiments, the cationic peptide may be linked to another peptide that does not qualify as a cationic peptide and/or to a non-amino acid or non-peptide component, such as, but not limited to, a lipid, a fatty acid, a carbohydrate or a nucleic acid. In certain non-limiting embodiments the cationic peptide may be conjugated to one or more additional molecule, for example, but not limited to, a carbohydrate, an antibiotic, an antiproliferative agent, a pharmaceutical, or another peptide, whose physiochemical properties makes them impermeable across urothelium.

An "anionic agent" is an agent that may be used as a diagnostic or therapeutic wherein at least a portion of the agent has a negative charge that can form a non-covalent attachment with a cationic peptide. In certain, non-limiting embodiments, the anionic agent is an antisense oligonucleotide. In certain, non-limiting embodiments, the antisense oligonucleotide is at least about 10 nucleic acids long, or at least about 15 nucleic acids long, or at least about 20 nucleic acids long, or at least about 25 nucleic acids long, or up to about 30 nucleic acids long, or up to about 50 nucleic acids long, or up to about 75 nucleic acids long, or up to about 100 nucleic acids long, or between about 15 and 75 nucleic acids long, or between about 15 and 40 nucleic acids long. In certain non-limiting embodiments, the antisense oligonucleotide inhibits the expression/reduces the level of nerve growth factor. In certain non-limiting embodiments, said nerve growth factor is human nerve growth factor encoded by a mRNA having a corresponding cDNA sequence set forth in GenBank Accession No. GenBank: M57399.1, as follows:
1 tctgcttta ataagcttcc caatcagctc tcgagtgcaa agcgctctcc ctccctcgcc
61 cagccttcgt cctcctggcc cgctcctctc atccctccca ttctccattt ccct-tccgtt
121 ccctccctgt cagggcgtaa ttgagtcaaa ggcaggatca ggttcccgc cttccagtcc
181 aaaaatcccg ccaagagagc cccagagcag aggaaaatcc aaagtg-gaga gaggggaaga
241 aagagaccag tgagtcatcc gtccagaagg cggggagagc agca-gcggcc caagcaggag
301 ctgcagcgag ccgggtacct ggactcagcg gtagcaacct cgc-cccctgc aacaaaggca
361 gactgagcgc cagagaggac gtttccaact caaaaatgca ggct-caacag taccagcagc
421 agcgtcgaaa atttgcagct gccttcttgg cattcatttt catactggca gctgtggata
481 ctgctgaagc agggaagaaa gagaaaccag aaaaaaaagt gaagaagtct gactgtggag
541 aatggcagtg gagtgtgtgt gtgcccacca gtggagactg tgggctgggc acacgggagg
601 gcactcggac tggagctgag tgcaagcaaa ccatgaagac ccaga-gatgt aagatccct
661 gcaactggaa gaagcaattt ggcgcggagt gcaaatacca gttccag-gcc tggggagaat
721 gtgacctgaa cacagccctg aagaccagaa ctggaagtct gaagc-gagcc ctgcacaatg
781 ccgaatgcca gaagactgtc accatctcca agccctgtgg caaactgacc aagcccaaac
841 ctcaagcaga atctaagaag aagaaaaagg aaggcaagaa acagga-gaag atgctggatt
901 aaaagatgtc acctgtggaa cataaaaagg acatcagcaa acag-gatcag ttaactattg
961 catttatatg taccgtaggc tttgtattca aaaattatct atagctaagt aca-caataag
1021 caaaaacaa [SEQ ID NO:9],
and said antisense oligonucleotide is homologous to a portion thereof which is at least about 10 nucleic acids long, or at least about 15 nucleic acids long, or at least about 20 nucleic acids long, or at least about 25 nucleic acids long, or up to about 30 nucleic acids long, or up to about 50 nucleic acids long, or up to about 75 nucleic acids long, or up to about 100 nucleic acids long, or between about 15 and 75 nucleic acids long, or between about 15 and 40 nucleic acids long. As non-limiting examples, analogous antisense oligonucleotides may be directed to mRNAs encoding Vascular Endothelial Growth Factor ("VEGF"), transforming growth factor-beta1 ("TGF-β1"), Brain Derived Neurotrophic Factor (BDNF), neurotrophin-4/5 (NT-4/5), cell cycle protein involved in cell proliferation and migration such as onco-protein-18/stathmin 1 or PIK-1, inflammatory proteins, cytokines, chemokines, caspase-1, or proteins involved in autophagy such as microtubule-associated protein 1 light chain 3 (LC3B), autophagy protein 5 ATG5, beclin 1, LAMP-2, for example but not limited to human Vascular Endothelial Growth Factor ("VEGF"), transforming growth factor-beta1 ("TGF-β1"), Brain Derived Neurotrophic Factor (BDNF), neurotrophin-4/5 (NT-4/5), cell cycle protein involved in cell proliferation and migration such as onco-protein-18/stathmin 1 or PIK-1, inflammatory proteins, cytokines, chemokines, caspase-1, or proteins involved in autophagy such as microtubule-associated protein 1 light chain 3 (LC3B), autophagy protein 5 ATG5, beclin 1, LAMP-2.

In certain, non-limiting embodiments, the anionic agent is an interfering RNA (siRNA) oligonucleotide. In certain, non-limiting embodiments, the siRNA oligonucleotide is at least about 10 nucleic acids long, or at least about 15 nucleic acids long, or at least about 20 nucleic acids long, or at least about 25 nucleic acids long, or up to about 30 nucleic acids long, or up to about 50 nucleic acids long, or up to about 75 nucleic acids long, or up to about 100 nucleic acids long, or between about 15 and 75 nucleic acids long, or between about 15 and 40 nucleic acids long. In certain non-limiting embodiments, the siRNA oligonucleotide inhibits the expression/reduces the level of nerve growth factor. In certain non-limiting embodiments, said nerve growth factor is human nerve growth factor encoded by a mRNA having the corresponding cDNA sequence set forth in GenBank Accession No. GenBank: M57399.1 (for example SEQ ID NO:9 above) and said siRNA oligonucleotide is homologous to a portion thereof which is at least about 10 nucleic acids long, or at least about 15 nucleic acids long, or at least about 20 nucleic acids long, or at least about 25 nucleic acids long, or up to about 30 nucleic acids long, or up to about 50 nucleic acids long, or up to about 75 nucleic acids long, or up to about 100 nucleic acids long, or between about 15 and 75 nucleic acids long, or between about 15 and 40 nucleic acids long. As non-limiting examples, analogous siRNA oligonucleotides may be directed to mRNAs encoding Vascular Endothelial Growth Factor ("VEGF"), transforming growth factor-beta1 ("TGF-β1"), Brain Derived Neurotrophic Factor (BDNF), neurotrophin-4/5 (NT-4/5), cell cycle protein involved in cell proliferation and migration such as oncoprotein-18/stathmin 1 or PIK-1, inflammatory proteins, cytokines, chemokines, caspase-1, or proteins involved in autophagy such as microtubule-associated protein 1 light chain 3 (LC3B), autophagy protein 5 ATG5, beclin 1, LAMP-2, for example but not limited to human Vascular Endothelial Growth Factor ("VEGF"), transforming growth factor-beta1 ("TGF-β1"), Brain Derived Neurotrophic Factor (BDNF), neurotrophin-4/5 (NT-4/5), cell cycle protein involved in cell proliferation and migration such as oncoprotein-18/stathmin 1 or PIK-1, inflammatory proteins, cytokines, chemokines, caspase-1, or proteins involved in autophagy such as microtubule-associated protein 1 light chain 3 (LC3B), autophagy protein 5 ATG5, beclin 1, LAMP-2.

Such antisense or siRNA oligonucleotides may comprise non-naturally occurring bases or linkages as are known in the art, for example, but not limited to, phosphorothioate residues, 2'-O-methyl (2'-O-Me) phosphorothioate, 2'-O-methoxyethyl (2'-O-MOE) phosphorothioate residues, Oligodeoxyribonucleotides with phosphonoacetate or thiophosphonoacetate internucleotide linkages, locked nucleic acids, and/or synthehic microRNA, short hairpin RNA, small interfering RNA, piwi-associated RNAs negatively charged homo-oligomers of alternating trans-4-hydroxy-L-proline/phosphonate polyamides (HypNA-pPNA)

Other anionic compounds that may be used as therapeutic or diagnostic agents include Bacille Calmette-Guerin cell wall skeleton, suramin and (polysulfonated naphtylurea), plasmid DNA, anionic peptides, anionic antifungal peptides.

In certain non-limiting embodiments, the invention provides for a pharmaceutical composition comprising said cationic peptide(s) and anionic agent(s) for intravesical administration to a subject (a delivery formulation). Said composition may be available as such or may be prepared shortly before administering to the subject by mixing the cationic peptide(s) with the anionic agent(s) or by reconstituting a mixture of the two. In one specific non-limiting embodiment, the cationic peptide mixture is a commercially available protamine injection solution which is mixed with the anionic agent prior to administering to the subject.

In other non-limiting embodiments, the cationic peptide(s) and the anionic agent are provided as separate components in a kit, to be mixed together to form a delivery formulation shortly before administering to a subject. "Shortly before" means within about 30 days prior to use or within about one week prior to use or within about 3 days prior to use or within about 2 days prior to use or within about 24 hours prior to use or within about 12 hours prior to use or within about 8 hours prior to use.

In certain non-limiting embodiments, the present invention provides for a mixture that may comprise a therapeutic or diagnostic oligonucleotide in the concentration range of 2-20 micromolar mixed with cationic peptide or cationic peptide mixture (eg protamine sulfate) in the 20-200 micromolar range. In certain non-limiting embodiments, the cationic peptide is protamine and the concentration of protamine is less than 10 mg/mL, or less than 1 mg/mL, or less than 0.6 mg/mL, or less than 0.4 mg/mL, or between 0.2 mg/mL and 0.6 mg/mL, or between about 0.2 mg/mL and 0.4 mg/mL, or about 0.3 mg/mL, or about 0.4 mg/mL.

In certain non-limiting embodiments, the weight ratio of cationic peptide(s) to anionic agent is between about 1:1 to about 40:1 or between about 5:1 to about 30:1 or between about 5:1 to about 15:1 and/or may be about 1:1 or about 5:1 or about 10:1 or about 15:1 or about 20:1 or about 30:1 or about 40:1.

In certain non-limiting embodiments, the weight ratio of protamine sulfate to oligonucleotide is between about 1:1 to about 40:1 or between about 5:1 to about 30:1 or between about 5:1 to about 15:1 and/or may be about 1:1 or about 5:1 or about 10:1 or about 15:1 or about 20:1 or about 30:1 or about 40:1.

The pharmaceutical compositions of the invention may further comprise one or more pharmaceutically suitable solvent, such as but not limited to water and/or saline, and may optionally comprise one or more additional therapeutic or diagnostic agent.

In certain non-limiting embodiments the present invention provides for a method of treating a subject, in need of such treatment, with an anionic therapeutic agent, comprising administering into the bladder of the subject an effective amount of an anionic therapeutic agent in combination with a cationic peptide(s) in an amount that promotes the uptake of the therapeutic agent into bladder cells. In non-limiting embodiments, the subject may be suffering from overactive bladder ("OAB"), bladder cancer, or interstitial cystitis.

In certain non-limiting embodiments the present invention provides for a method of performing a diagnostic procedure on the bladder of a subject, comprising administering into the bladder of the subject an effective amount of an anionic diagnostic agent in combination with a cationic peptide(s) in an amount that promotes the uptake of the diagnostic agent into bladder cells, thereby enabling the diagnostic procedure. As a non-limiting example, the diagnostic procedure may be an imaging procedure and the anionic agent may be an imaging dye, whereby the method enhances the ability of the dye to produce an image of the urothelium.

In certain non-limiting embodiments the present invention provides for a method of treating a subject with overactive bladder, comprising administering into the bladder of the subject a therapeutic amount of an antisense oligonucleotide toward nerve growth factor in combination with a cationic peptide(s) in an amount that promotes the uptake of the antisense oligonucleotide into bladder cells to reduce the level of nerve growth factor and reduce the frequency of urination and/or feeling of urgency to urinate. In a specific non-limiting embodiment the cationic peptide(s) is a mixture of cationic peptides as comprised in a protamine solution.

A subject may be a human or a non-human subject, including but not limited to a non-human primate, a rodent, a rabbit, a dog, a cat, a horse, a goat, a cow or bull, a sheep, or a bird.

WORKING EXAMPLE

The present study describes the use of a new carrier for ODN, Protamine, which has been used as a component in the delivery system for gene and ODN in the past, but not in this context [14]. Protamine is highly stable, well characterized and is used clinically as an antidote to heparin overdoses and a complexing agent for insulin in long-acting preparations [15]. It has, however, been reported to have toxic effects when instilled into bladder at relatively higher concentration [21-23].

A. Methods

Oligonucleotides: The 18mer phosphorothioated antisense oligonucleotide (ODN) was used in all experiments with the sequence 5'GCCCGAGACGCCTCCCGA 3' (SEQ ID NO: 10), which was directed against unique sequence in exon 3 of rat NGF mRNA and was custom made by Integrated DNA technologies (San Diego, Calif.). ODN had a 5' tag of TYE™ 563 for uptake studies. Stock solution of HPLC grade ODN was prepared at 2 mM in nuclease free distilled water (Invitrogen, Grand Island, N.Y., USA).

Protamine: Protamine sulfate Grade X, was purchased from Sigma (Catalog P4020) with a molecular mass of approx. 5.1 KDa and stock solution was prepared at 5 mg/mL. Aliquots of ODN solution containing 5 μg/mL were mixed in mass ratios ranging from 1:1 to 1:40 with aqueous solutions of Protamine sulfate 5-200 μg/mL. The binary complex was incubated at room temperature for 30 minutes prior to experiments and prepared fresh before every experiment.

Cell lines and cell culture: UROtsa cell line was maintained in a humidified incubator containing 5% $CO_2$-95% atmospheric air at 37° C. in Minimum Essential Medium (Thermo Fisher Scientific, Pittsburgh, Pa.) supplemented with 10% (v/v) fetal bovine serum and 1% (v/v) antibiotic/antimycotic (Catalog Number 15240, Invitrogen).

Intracellular uptake of TYE™-labeled ODN-10,000 cells of UROtsa cell line were plated in an eight-well tissue culture chamber slides made of glass (Falcon, Becton Dickinson, N.Y.) at 37° C. and after 19 h, plated cells were treated with 5 μg/mL of TYE™ 563-labeled ODN or the binary complex containing ODN complexed with protamine 5-200 μg/mL in different mass ratios. All preparations were diluted 2-fold with incomplete media and incubated for 4 hours. After 4 hours, cells were washed to remove residual ODN preparations and then incubated with complete media for 19 h. After incubation, cells were washed three times with cold PBS and were fixed with a 5% (w/w) solution of paraformaldehyde in PBS for 7 min and then embedded in an antifading substance. Images were taken with a fluorescence microscope equipped with a laser (BX51, Olympus America Inc, Center Valley, Pa.,) and image digitized by Magnafire. All optical sections were recorded at the same exposure time and images were processed with the Image software.

Cell viability: 10,000 cells were seeded in 96-well culture plates and after 19 h, the medium was replaced with incomplete medium containing different concentrations of prepared ODN protamine complexes for 4 h. The cell media was replaced after ODN exposure with complete culture medium for the next 19 h. 3-(4,5-dimethylthiazol-2-yl)-2,5-diphenyltetrazolium bromide salt (5 mg/mL of stock in PBS) was then added (10 µl per well in 100 ml) and plate was further incubated for 5 h. At the end of the incubation period, the reaction mixture was carefully removed and 200 µl of culture grade DMSO was added to each well. The plates were kept on rocker shaker for 10 min at room temperature and then analyzed at 550 nm using multi well micro plate reader (Synergy HT, Bio-Tek, USA). Unexposed sets were also run under identical conditions and served as untreated controls.

Bladder uptake studies: Rats were anesthetized with 2% isoflurane and their bladders were catheterized by 24-gauge angiocatheters (Becton Dickinson), washed with saline to instill 0.5 mL of fluorescent TYE™ conjugated ODN dissolved in nuclease free water or complexed with protamine for 60 min. Rats restarted their voiding in metabolic cages at the end of instillation. Bladders were harvested at the time of sacrifice and cryopreserved for cryosectioning into 8 micron thick tissue sections. Sections were examined for fluorescence signal by fluorescence microscope equipped with a laser.

Efficacy studies: 13 rats were anesthetized with 2% isoflurane and 24-gauge angiocatheters were inserted into their urethras. Via these catheters, urine was drained from the bladders and phosphorothioated NGF antisense ODN (2-12 µM) complexed with protamine (n-5), in a volume of 0.5 ml, was instilled. The sham group received saline or protamine sulfate 0.3 mg/mL (n=4) and a control group without any instillation was also included for saline cystometry 24 h after instillation under urethane anesthesia (1.0 g/kg, s.c.). The efficacy of instilled treatments were assessed by comparing results of saline with acetic acid cystometry 0.25% v/v acetic acid in saline infusion at the rate of 0.04 mL/min. A polyethylene catheter (PE-50) was connected by a three-way stopcock to a pressure transducer and to a syringe pump. The catheter was then inserted into the bladder transurethrally for recording intravesical pressure and for infusing solutions into the bladder. The intravesical pressure was recorded with data-acquisition software (sampling rate 400 Hz; Chart) on a computer system equipped with an analog-to-digital converter. The rats' body temperatures were maintained in the physiologic range using a heating lamp. A control CMG was performed by slowly filling the bladder with saline (0.04 mL/min) to elicit repetitive voiding for more than for 1 hour. Subsequently, bladder irritation was induced by 0.25% AA infusion. The ICI of the reflex bladder contractions during saline and AA was determined as the time between 2 continuing contraction cycles. The average of at least 3 ICIs measured for more than 30 min after saline infusion and 60 min after AA infusion, respectively was compared.

Immunohistochemistry: Following cystometry, bladders were cryopreserved and 8 µm thick cryosections were washed in PBS and pre-incubated with PBS containing 20% normal serum (Jackson lmmunoresearch) and 0.2% Triton X-100 (VWR International,) for 2 h at room temperature. The primary polyclonal rabbit H-20 antibody (1:50) (Santa Cruz Biotechnology, Santa Cruz, Calif.) for NGF was applied in PBS containing 5% normal serum, 0.2% Triton X-100 for 16-18 h at 4° C. Sections were washed in PBS containing 0.1% BSA, 0.1% Triton X-100, 4× for 5 min each at room temperature. The secondary donkey anti-rabbit Alexa Fluor 488 (1:200) (Molecular Probes, Eugene, Oreg.) antibody was applied for 2 h at room temperature in PBS containing 0.1% BSA, 0.1% Triton X-100. Washing was performed 3× at room temperature in PBS, and sections were mounted with an aqueous mounting medium. Immunostaining was analyzed with a Nikon confocal microscope.

NGF levels in harvested bladders: The rat bladders were harvested at the end of cystometry. Tissues were homogenized in RIPA lysis buffer system (Santa Cruz Biotechnology Inc., USA) in the presence of 1 mM $Na_3VO_4$, 2 mM PMSF and 10 µL/mL protease inhibitor cocktail. Protein was estimated using pierce BCA protein Assay kit (Thermo Scientific, USA). Tissue lysates were stored at −20° C. until assay and assayed in triplicate in an antigen capture ELISA Emax Immuno-Assay System (Promega, Madison, Wis.) according to the manufacturer's instructions. ELISA plates were read at 450 nm on an Elx800 microplate reader (Bio-Tek Instruments, Winooski, Vt.). Tissue NGF values were normalized against the protein concentrations of each sample and expressed as picograms per milligram of protein.

Figure 2:
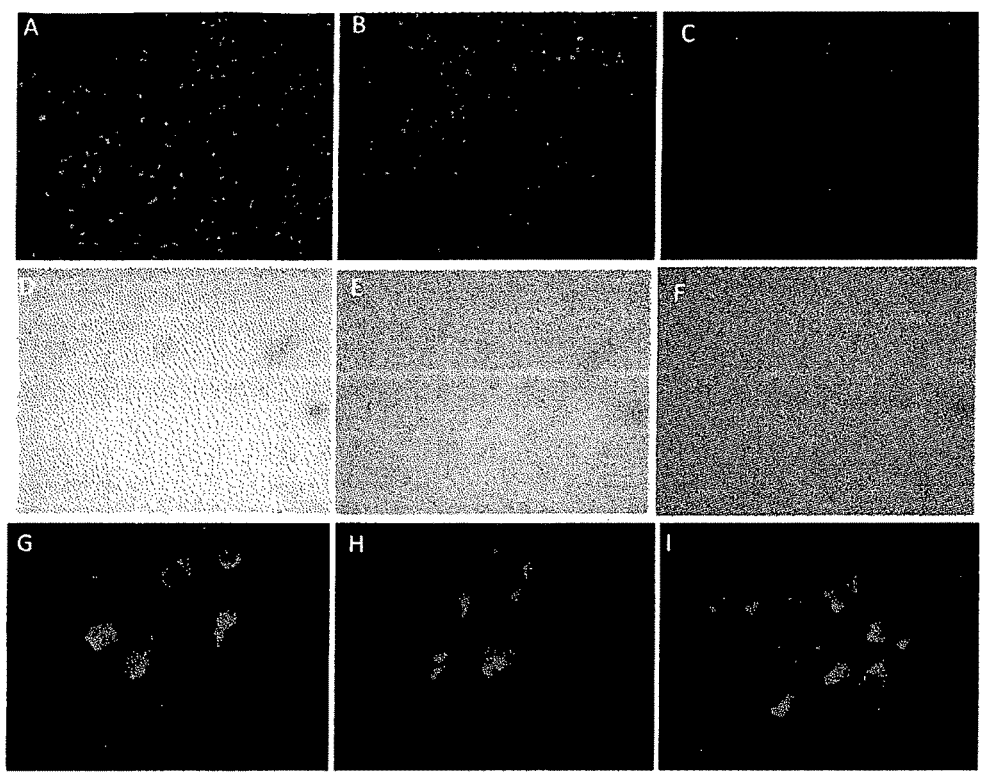
FIG. 2A-I: Cellular uptake studies of ODN: Uptake of fluorescent oligonucleotide by uroepithelium cells in culture at higher protamine: oligonucleotide ratios. UROtsa cells were incubated for 4 h at 37° C. with (A) 5'-TYE™ 563 labelled Phosphorothioate oligonucleotide and protamine in 1:10, (B) 1:20 (C) 1:40 ODN/protamine particles. Cells were washed at the end of 4 h exposure to ODN mixture and the fluorescent images were captured following further incubation of treated cells for 24 hours at 37° C. Respective bright field images are shown in panels, D, E and F. The amount of fluorescent oligonucleotide added to each well was always 1 μg and the protamine amount varied from 10, 20 and 40 μg in panels A, B and C, respectively. Exposure time was constant in all images at 1.2 sec in panels A, B and C with magnification 10× and corresponding images at higher magnification for each panel are shown in panels G, H and I.

B. Results:

Cellular uptake studies: Cellular uptake was investigated by incubating naked and ODN complexed with protamine at 37° C. for 4 hours and assessing the fluorescent signal in cells 24 h later. Cells treated with ODNs in the absence of protamine showed absence of any fluorescent signal (FIG. 1A). In contrast, all protamine/ODN complexes showed protamine concentration dependent increase of ODN uptake. The highest efficacy was found with increasing mass ratios (FIGS. 1&2). At the mass ratio 1:5 the cells seemed to be full of ODN and uptake increased up to 1:10 ratio and cellular toxicity was observed at higher concentration.

Images taken at higher magnification demonstrate that protamine nanoparticles formed with ODN were localized in the nucleus (FIG. 2G-I). The binary complex showed toxicity at higher concentration of protamine sulfate in FIG. 1 bottom panel as revealed by decrease in cell viability relative to control untreated cells represented by 0 µg on x-axis. Higher concentration of protamine reduced cell viability. Protamine sulfate induced toxicity is also related to reduced fluorescence (FIGS. 2C & F). Although cellular uptake and subcellular localization of fluorescent ODN is visible at higher magnification (FIG. 2G-I), images taken at lower magnification showed the uniform uptake of binary complexes and were better in revealing toxicity from higher concentrations of protamine, for example 40 µg per well or 0.2 mg/mL.

Figure 3:
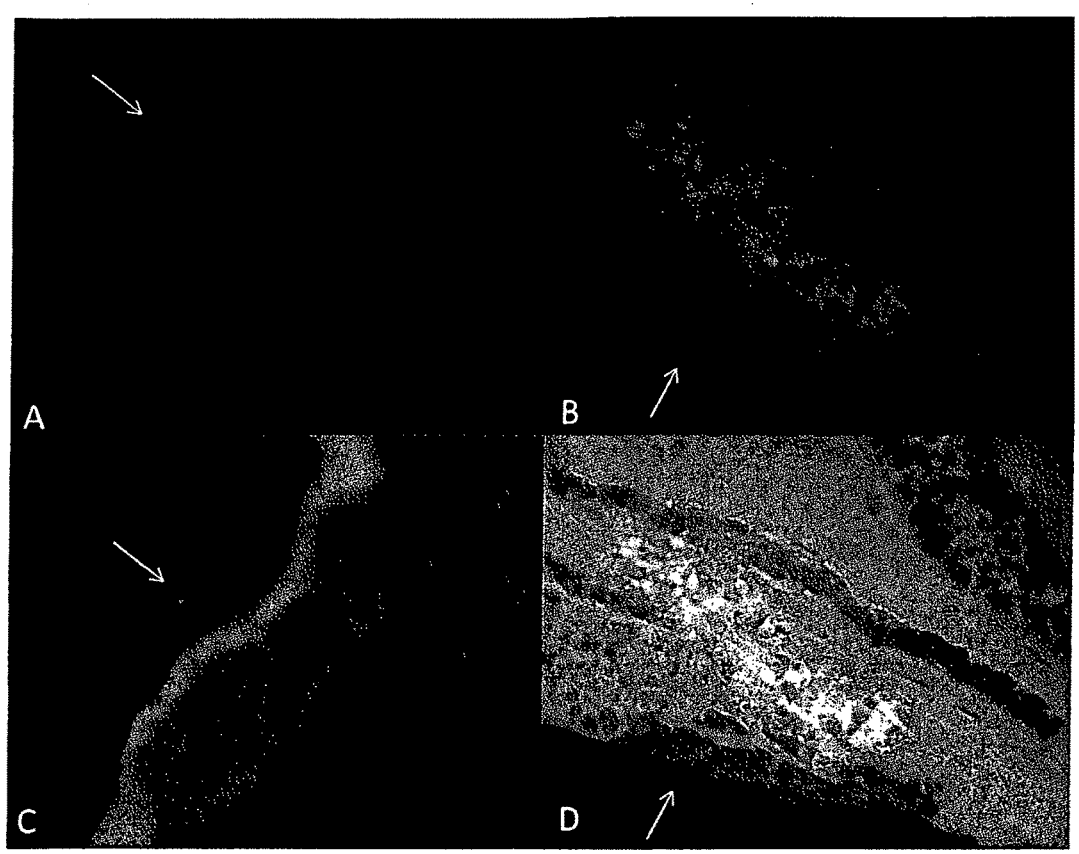
FIG. 3A-D: Bladder Uptake of ODN: Results of in vivo instillation of fluorescent oligonucleotide and protamine sulfate into rat bladder, showing fluorescence 24 hours later. Fluorescence images of rat bladders harvested 24 h post-instillation with antisense oligonucleotide with 5' tag of TYE™ 563 at 15 μg/mL complexed with 150 mg/mL protamine sulfate (panel A) and those instilled with ODN 30 μg/mL complexed with 300 μg/mL of protamine sulfate (panel B). The bright red fluorescence demonstrates successful uptake and retention in target cells of ODN delivered by protamine and higher concentration of ODN led to deeper penetration of ODN into the bladder (panel B). Fluorescence integrated intensity images are shown in respective sections to confirm the source of red fluorescent signal. Lumen side of the section is marked by a white arrow. Magnification is 10× in all sections.

Bladder Uptake: Rat bladders harvested after ODN instillation were cryosectioned for viewing the red fluorescence under the microscope (FIG. 3) The fluorescent signal was used as a measure of bladder uptake of ODN after instillation. Protamine mediated bladder uptake of ODN was evident from intense fluorescence of TYE™ 563 in bladder sections. Increasing the dose of TYE™ 563 labeled ODN, while keeping the mass ratio of ODN:protamine 1:10, increased the intensity of fluorescence in bladder. Our previous studies have demonstrated the naked ODN at the concentration of 15 µg/mL (or 0.015 mg/mL) does not transfer into the bladder cells[7]. Fluorescence integrated intensity images are shown below the fluorescent images to reveal the localization of fluorescent signal.

Figure 4:
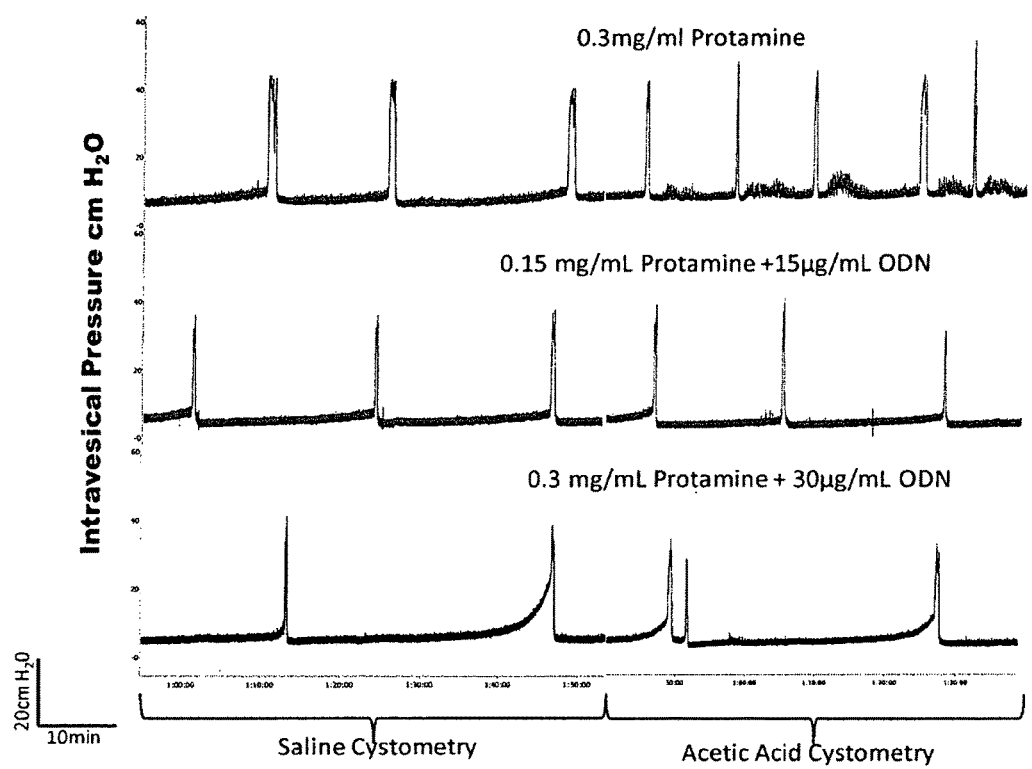
FIG. 4: Functional Effect of ODN Carried By Protamine: Cystometric analysis of bladder overactivity in treated groups induced by intravesical application of acetic acid ("AA"; 0.25%). Top tracing: Representative CMG was performed 24 h post-instillation of 0.3 mg/mL protamine (sham group), binary complex of antisense ODN (15 µg) and protamine (middle trace) and antisense ODN (30 µg) complexed with protamine (bottom trace). Baseline CMG (60 min prior to acetic acid infusion) and post-acetic acid cystometry are shown in left and right traces, respectively. Note that the AA-induced reduction in ICI was seen in a rat not treated with ODN (top tracing), but not in the group treated with NGF antisense complex with protamine to demonstrate the protective effect of antisense ODN. CMG parameters in absence of AA were not significantly different between groups.

Cystometry: Baseline CMG under saline infusion was indistinct between the groups. Pretreatment of antisense ODN (n=4) complexed with protamine blocked the AA induced bladder overactivity (FIG. 4A, middle and bottom tracing). The sequence specificity of NGF antisense ODN selected for these experiments has been demonstrated previously, with scrambled ODN sequence not showing any effect [7] in this model. The ICI was longer in the antisense treated group, compared to the sham group and the differences were statistically significant using one-way ANOVA followed by Tukey's post test (*p<0.05) (FIG. 4B).

Figure 5:
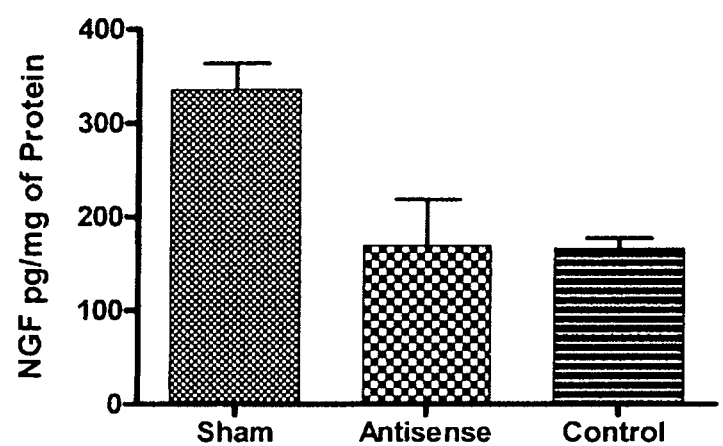
FIG. 5: Effect on Bladder NGF levels: Bladder tissue harvested from each group was analyzed for NGF levels measured by ELISA (n=4). Exposure to acetic acid ("AA") raised the NGF levels in sham group compared to control group that was not exposed to AA. Pretreatment with NGF antisense complexed with protamine (30 µg/mL) blunted the AA induced rise in NGF levels. ANOVA followed by Tukey's test showed significant reduction of NGF expression in rat group treated with NGF antisense (30 µg/mL) (*P<0.05)

Bladder NGF levels: AA exposure elevated the NOF production in the sham group relative to the control group. Pretreatment with NGF antisense ODN significantly blocked the AA induced NGF overexpression in the tissue lysates of bladder (FIG. 5). Results of FIG. 5 can be directly inferred from the bladder uptake of ODN facilitated by protamine. NGF levels in control rat group not exposed to AA were not raised.

C. Discussion

A carrier for therapeutic oligonucleotides that is easy to make and instill in the bladder for in viva experiments as described here has translation potential for patients that are refractory to traditional treatment of overactive bladder ("OAB"), bladder cancer or interstitial cystitis. Protamine is a natural and arginine-rich polycationic peptide of ~5.1 KDa. It is found in male gametes, where it forms compact structures with DNA and facilitates DNA delivery to the egg nucleus after fertilization. Protamine possesses several amino acid sequences resembling that of a nuclear localization signal[14], which may facilitate DNA delivery to nucleus. It is non-antigenic[16], due to the lack of aromatic amino acids and the lack of a rigid structure[17]. We hypothesized that cationic protamine can self-assemble with the anionic ODN, forming a stable complex, which facilitates the bladder uptake of ODN.

In earlier experiments protamine was shown to form nanoparticles with ODN [18, 19] in the size range of 100-200 nm. The ratio of bound ODN and number of particles increased with increasing mass ratio of protamine in the binary complex [10]. Binary complexes at mass ratios higher than 1:2 showed positive surface potentials [20] due to excess amounts of cationic peptide. However those observations were only from cell culture and the complexes were yet to be tested in animals, an essential prerequisite for assessing potential clinical benefit.

The observations described here are unexpected, when considered in the light of the reports describing toxic effects of protamine when instilled into the bladder at relatively higher concentration [21-23]. High concentrations of protamine sulfate 10-30 mg/mL [24] induce damage to the bladder epithelium in animals that mimics the damage to urothelium in interstitial cystitis patients. However, lower concentrations of protamine sulfate were deemed to be safe in the animal experiments as permeability of rat bladder instilled with protamine sulfate at 1 mg/mL [25] was not different from rat bladder instilled with saline. Bladder uptake studies of ODN and efficacy studies shown in FIG. 3-5 used protamine sulfate the lower concentration of 0.3 mg/mL.

It is known that bladder permeability in the ex vivo setup does not mimic the observation made in the in vivo setup as the former is vulnerable to effects of ischemia and mediators released from excised bladder[26]. This is an important point to consider when interpreting the results from Using chamber studies involving excised rabbit bladder, where protamine sulfate at 0.1 mg/mL increased the apical membrane conductance for cations [27, 28]. In fact, results of excised rabbit bladder are consistent with our cell culture experiments, where we found that protamine sulfate at concentrations higher than 0.2 mg/mL was toxic to the UROtsa cells. Taken together, it can be easily inferred that cultured cells and excised bladder cannot mimic the barrier function erected inside the intact bladder of a live animal.

The optimum mass ratio of 1:10 (ODN:protamine) found from cell culture experiments for complexation of ODN with protamine sulfate was maintained for animal experiments. Following that ratio, 0.3 mg/mL of protamine sulfate was used as a carrier to deliver up to 0.03 ng/mL of ODN to rat bladder. The concentration of 0.3 mg/mL for protamine sulfate is much lower than the concentration of 1 mg/mL found safe in rat [29] and rabbit [25] in vivo experiments. Consistent with earlier reports, we did not observe any toxicity from instilling protamine sulfate at 0.3 mg/mL in absence of ODN in control group. Furthermore, our culture experiments also justify use of 1:5 mass ratio, which permits use of protamine at 0.15 mg/mL, if necessary for future experiments with cystitis rat model with compromised bladder barrier.

Based on earlier reports, an energy dependent uptake mechanism based on endocytosis is assumed for cellular uptake of protamine+ODN complex [30]. Interaction of cationic peptide with the anionic residues on the cell surfaces seems important for adsorption on cell membranes and internalization. Protamine is considered to facilitate delivery by allowing ODN to escape endocytic vesicles, lysosomal degradation, and its translocation into the nucleus. Present study substantiates the therapeutic potential of the NGF antisense in cell culture and animal experiments.

Bladder instillation of antisense ODN can be an efficient means to control the expression of therapeutically relevant genes and elucidate the functional role of newly discovered genes in bladder function. Nerve growth factor has emerged as an attractive drug target for OAB [31] and its downregulation with antisense ODN is an potential approach[7]. Recently cationic liposomes have been demonstrated to be effective in intravesical delivery of ODN[7]. However, cationic liposomes will require further modification to curb their cytotoxicity [32] in the event that cystoscope-guided intradetrusor injection into bladder is considered for prolonged duration of action and in treatment of refractory patients. Protamine sulfate in the concentrations of about 0.3 mg/mL used here is less cytotoxic than cationic lipids used in liposomal formulation (7 mg/mL) for intradetrusor injection.

Various viral and nonviral delivery strategies are being developed for improved gene delivery. However, viral approaches are hindered by side effects such as immunogenicity and toxicity, whereas nonviral delivery systems have limited transfection efficiency and biodegradability issues [33]. Protamine and ODN can be simply mixed together and rapidly delivered, without cumbersome steps attendant to many other types of vectors such as liposomes and polymers or other tools of nanotechnology. The formulation is particularly well suited for localized use, particularly intravesical instillation in the safe dose range for delivery of therapeutic ODN against NGF in treatment of interstitial cystitis, overactive bladder.

Conclusions: Protamine is an effective carrier for delivering therapeutic ODN to bladder. It non-covalently binds to form a liquid complex for easy instillation into bladder.

7. REFERENCES

1. Dadgostar, H. and N. Waheed, *The evolving role of vascular endothelial growth factor inhibitors in the treatment of neovascular age-related macular degeneration.* Eye, 2008. 22(6): p. 761-7.
2. Tyagi, P., M. P. Kashyap, N. Kawamorita, T. Yoshizawa, M. Chancellor, and N. Yoshimura, *Intravesical Liposome and Antisense Treatment for Detrusor Overactivity and Interstitial Cystitis/Painful Bladder Syndrome.* ISRN Pharmacol, 2014. 2014: p. 601653.
3. Dadgostar, H. and N. Waheed, *The evolving role of vascular endothelial growth factor inhibitors in the treatment of neovascular age-related macular degeneration.* Eye (Lond), 2008. 22(6): p. 761-7.
4. Gebhard, C., G. Huard, E. A. Kritikou, and J. C. Tardif, *Apolipoprotein B Antisense Inhibition-Update on Mipomersen.* Curr Pharm Des, 2013. 19(17): p. 3132-42.
5. Blietz, C. E., B. Thode, M. Hauses, R. Pries, A. J. Meyer, C. Doehn, D. Jocham, and I. Kausch, *In vivo studies on the availability and toxicity of antisense oligonucleotides in bladder cancer.* In Vivo, 2009. 23(1): p. 13-9.
6. Martin, T. A. and W. G. Jiang, *Loss of tight junction barrier function and its role in cancer metastasis.* Biochim Biophys Acta, 2009. 1788(4): p. 872-91.
7. Kashyap, M., N. Kawamorita, V. Tyagi, Y. Sugino, M. Chancellor, N. Yoshimura, and P. Tyagi, *Downregulation of NGF Expression in the Bladder by Antisense Oligoucleotides as New Treatment for Overactive Bladder.* J Urol, 2013. 190(2):757-64.
8. Nogawa, M., T. Yuasa, S. Kimura, M. Tanaka, J. Kuroda, K. Sato, A. Yokota, H. Segawa, Y. Toda, S. Kageyama, T. Yoshiki, Y. Okada, and T. Maekawa, *Intravesical administration of small interfering RNA targeting PLK-1 successfully prevents the growth of bladder cancer.* J Clin Invest, 2005. 115(4): p. 978-85.
9. Martin, D. T., J. M. Steinbach, J. Liu, S. Shimizu, H. Z. Kaimakliotis, M. A. Wheeler, A. B. Hittelman, W. Mark Saltzman, and R. M. Weiss, *Surface-modified nanoparticles enhance transurothelial penetration and delivery of survivin siRNA in treating bladder cancer.* Mol Cancer Ther, 2014. 13(1): p. 71-81.
10. Bunnell, B. A., F. K. Askari, and J. M. Wilson, *Targeted delivery of antisense oligonucleotides by molecular conjugates.* Somat Cell Mol Genet, 1992. 18(6): p. 559-69.
11. Tyagi, P., R. Banerjee, S. Basu, N. Yoshimura, M. Chancellor, and L. Huang, *Intravesical antisense therapy for cystitis using TAT-peptide nucleic acid conjugates.* Mol Pharm, 2006. 3(4): p. 398-406.
12. Uhlmann, E., A. Ryte, and A. Peyman, *Studies on the mechanism of stabilization of partially phosphorothioated oligonucleotides against nucleolytic degradation.* Antisense Nucleic Acid Drug Dev, 1997. 7(4): p. 345-50.
13. Wojcik, M., M. Cieslak, W. J. Stec, J. W. Goding, and M. Koziolkiewicz, *Nucleotide pyrophosphatase/phosphodiesterase 1 is responsible for degradation of antisense phosphorothioate oligonucleotides.* Oligonucleotides, 2007. 17(1): p. 134-45.
14. Sorgi, F. L., S. Bhattacharya, and L. Huang, *Protamine sulfate enhances lipid-mediated gene transfer.* Gene Ther, 1997. 4(9): p. 961-8.
15. Hansen, B., S. Linde, K. Kolendorf, and F. Jensen, *Absorption of protamine-insulin in diabetic patients. I. Preparation and characterization of protamine-125I-insulin.* Horm Metab Res, 1979. 11(2): p. 85-90.
16. Rodman, T. C., F. H. Pruslin, Y. Chauhan, S. E. To, and R. Winston, *Protamine-reactive natural IgM antibodies in human sera. Characterization of the epitope demonstrates specificity of antigenic recognition; occurrence indicates obscurity of origin and function.* J Exp Med, 1988. 167(3): p. 1228-46.
17. Tobita, T., M. Nomoto, M. Nakano, and T. Ando, *Isolation and characterization of nuclear basic protein (protamine) from boar spermatozoa.* Biochim Biophys Acta, 1982. 707(2): p. 252-8.
18. Lochmann, D., J. Weyermann, C. Georgens, R. Prassl, and A. Zimmer, *Albumin-protamine-oligonucleotide nanoparticles as a new antisense delivery system. Part 1: physicochemical characterization.* Eur J Pharm Biopharm, 2005. 59(3): p. 419-29.
19. Lochmann, D., V. Vogel, J. Weyermann, N. Dinauer, H. von Briesen, J. Kreuter, D. Schubert, and A. Zimmer, *Physicochemical characterization of protamine-phosphorothioate nanoparticles.* J Microencapsul, 2004. 21(6): p. 625-41.
20. Junghans, M., J. Kreuter, and A. Zimmer, *Phosphodiester and phosphorothioate oligonucleotide condensation and preparation of antisense nanoparticles.* Biochim Biophys Acta, 2001. 1544(1-2): p. 177-88.
21. Aydin, H., F. Ercan, S. Cetinel, and T. San, *Morphological examination of the effects of defibrotide on experimentally induced bladder injury and its relation to interstitial cystitis.* Urol Res, 2001. 29(4): p. 263-71.
22. Cetinel, S., F. Ercan, S. Sirvanci, O. Sehirli, Y. Ersoy, T. San, and G. Sener, *The ameliorating effect of melatonin on protamine sulfate induced bladder injury and its relationship to interstitial cystitis.* J Urol, 2003. 169(4): p. 1564-8.
23. Chuang, Y. C., M. B. Chancellor, S. Seki, N. Yoshimura, P. Tyagi, L. Huang, J. P. Lavelle, W. C. De Groat, and M. O. Fraser, *Intravesical protamine sulfate and potassium chloride as a model for bladder hyperactivity.* Urology, 2003. 61(3): p. 664-70.
24. Lavelle, J., S. Meyers, R. Ramage, S. Bastacky, D. Doty, G. Apodaca, and M. L. Zeidel, *Bladder permeability barrier: recovery from selective injury of surface epithelial cells.* Am J Physiol Renal Physiol, 2002. 283(2): p. F242-53.
25. Niku, S. D., P. C. Stein, H. C. Scherz, and C. L. Parsons, *A new method for cytodestruction of bladder epithelium using prolamine sulfate and urea.* J Urol, 1994. 152(3): p. 1025-8.
26. Li, S., Y. S. Juan, B. A. Kogan, A. Mannikarottu, R. Leggett, C. Schuler, and R. M. Levin, *Effects of inosine on response to in vitro hypoxia in absence of substrate on bladder dysfunction in adult rats.* Urology, 2009. 73(3): p. 661-4.
27. Tzan, C. J., J. R. Berg, and S. A. Lewis, *Mammalian urinary bladder permeability is altered by cationic proteins: modulation by divalent cations.* Am J Physiol, 1994. 267(4 Pt 1): p. C1013-26.
28. Tzan, C. J., J. Berg, and S. A. Lewis, *Effect of protainine sulfate on the permeability properties of the mammalian urinary bladder.* J Membr Biol, 1993. 133(3): p. 227-42.
29. Shioyama, R., Y. Aoki, H. Ito, Y. Matsuta, K. Nagase, N. Oyama, Y. Miwa, H. Akino, Y. Imamura, and O. Yokoyama, *Long-lasting breaches in the bladder epithelium lead to storage dysfunction with increase in bladder PGE2 levels in the rat.* Am J Physiol Regul Integr Comp Physiol, 2008. 295(2): p. R714-8.
30. Barthel, F., J. S. Remy, J. P. Loeffler, and J. P. Behr, *Gene transfer optimization with lipospermine-coated DNA.* DNA Cell Biol, 1993. 12(6): p. 553-60.
31. Jacobs, B. L., M. C. Smaldone, V. Tyagi, B. J. Philips, S. V. Jackman, W. W. Leng, and P. Tyagi, *Increased nerve* growth factor in neurogenic overactive bladder and interstitial cystitis patients. Can J Urol, 2010. 17(1): p. 4989-94.
32. Nguyen, L T., K. Atobe, J. M. Barichello, T. Ishida, and H. Kiwada, *Complex formation with plasmid DNA increases the cytotoxicity of cationic liposomes*. Biol Pharm Bull, 2007. 30(4): p. 751-7.
33. Elsabahy, M., A. Nazarali, and M. Foldvari, *Non-viral nucleic acid delivery: key challenges and future directions*. Curr Drug Deliv, 2011. 8(3): p. 235-44.
34. WO 2004087931 A1
35. WO 2002010201 A2
36. WO 2007069068 A2
37. Degols et al., 1989, Nucl. Acids Res. 17(22):9341-9350.
38. Hoffmann et al., 1990, Protein Expression and Purification, Volume 1, p. 127-133.
39. Kashyap et al., 2013, J. Urol. 190(2):757-764.
40. Leonetti et al., 1988, Gene 72: 323-332.

Various patents and publications are cited herein, the contents of which are hereby incorporated by reference herein in their entireties.

```
                        SEQUENCE LISTING

<160> NUMBER OF SEQ ID NOS: 10

<210> SEQ ID NO 1
<211> LENGTH: 51
<212> TYPE: PRT
<213> ORGANISM: Homo sapiens

<400> SEQUENCE: 1

Met Ala Arg Tyr Arg Cys Cys Arg Ser Gln Ser Arg Ser Arg Tyr Tyr
1               5                   10                  15

Arg Gln Arg Gln Arg Ser Arg Arg Arg Arg Arg Ser Cys Gln Thr
                20                  25                  30

Arg Arg Arg Ala Met Arg Cys Cys Arg Pro Arg Tyr Arg Pro Arg Cys
                35                  40                  45

Arg Arg His
        50

<210> SEQ ID NO 2
<211> LENGTH: 102
<212> TYPE: PRT
<213> ORGANISM: Homo sapiens

<400> SEQUENCE: 2

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
                20                  25                  30

Glu Gln Gly Leu Ser Pro Glu His Val Glu Val Tyr Glu Arg Thr His
                35                  40                  45

Gly Gln Ser His Tyr Arg Arg Arg His Cys Ser Arg Arg Arg Leu His
                50                  55                  60

Arg Ile His Arg Arg Gln His Arg Ser Cys Arg Arg Lys Arg Arg
65                  70                  75                  80

Ser Cys Arg His Arg Arg Arg His Arg Arg Gly Cys Arg Thr Arg Lys
                85                  90                  95

Arg Thr Cys Arg Arg His
                100

<210> SEQ ID NO 3
<211> LENGTH: 32
<212> TYPE: PRT
<213> ORGANISM: Oryzias latipes

<400> SEQUENCE: 3

Met Arg Arg Gln Ala Ser Leu Pro Ala Arg Arg Arg Arg Arg Val Arg
1               5                   10                  15

Arg Thr Arg Val Val Arg Arg Arg Arg Val Gly Arg Arg Arg His
                20                  25                  30
```

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Arg Arg Arg Arg Ser Ser Ser Arg Pro Ile Arg Arg Arg Arg
1               5                   10                  15

Arg Pro Arg Ala Ser Arg Arg Arg Arg Gly Gly Arg Arg Arg Arg
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Arg Arg Arg Arg Ser Ser Arg Arg Pro Val Arg Arg Arg Arg
1               5                   10                  15

Pro Arg Val Ser Arg Arg Arg Arg Arg Gly Gly Arg Arg Arg Arg
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Arg Arg Arg Arg Ser Ser Ser Arg Pro Val Arg Arg Arg Arg
1               5                   10                  15

Pro Arg Val Ser Arg Arg Arg Arg Gly Gly Arg Arg Arg Arg
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Arg Arg Arg Arg Ala Ser Arg Arg Ile Arg Arg Arg Arg Pro
1               5                   10                  15

Arg Val Ser Arg Arg Arg Arg Gly Gly Arg Arg Arg Arg
            20                  25                  30

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)

```
<223> OTHER INFORMATION: Gly, Val or Ala
<220> FEATURE:
<223> OTHER INFORMATION: See specification as filed for detailed
      description of substitutions and preferred embodiments

<400> SEQUENCE: 8

Arg Arg Arg Xaa Xaa Arg Arg Arg
1               5

<210> SEQ ID NO 9
<211> LENGTH: 1029
<212> TYPE: DNA
<213> ORGANISM: Homo sapiens

<400> SEQUENCE: 9
tctgctttta ataagcttcc caatcagctc tcgagtgcaa agcgctctcc ctccctcgcc      60
cagccttcgt cctcctggcc cgctcctctc atccctccca ttctccattt ccttccgtt     120 ccctccctgt cagggcgtaa ttgagtcaaa ggcaggatca ggttccccgc cttccagtcc    180
aaaaatcccg ccaagagagc cccagagcag aggaaaatcc aaagtggaga gaggggaaga    240
aagagaccag tgagtcatcc gtccagaagg cggggagagc agcagcggcc caagcaggag    300
ctgcagcgag ccgggtacct ggactcagcg gtagcaacct cgccccttgc aacaaaggca    360
gactgagcgc cagagaggac gtttccaact caaaaatgca ggctcaacag taccagcagc    420
agcgtcgaaa atttgcagct gccttcttgg cattcatttt catactggca gctgtggata    480
ctgctgaagc agggaagaaa gagaaaccag aaaaaaaagt gaagaagtct gactgtggag    540
aatggcagtg gagtgtgtgt gtgcccacca gtggagactg tgggctgggc acacgggagg    600
gcactcggac tggagctgag tgcaagcaaa ccatgaagac ccagagatgt aagatcccct    660
gcaactggaa gaagcaattt ggcgcggagt gcaaatacca gttccaggcc tggggagaat    720
gtgacctgaa cacagccctg aagaccagaa ctggaagtct gaagcgagcc ctgcacaatg    780
ccgaatgcca aagactgtc accatctcca gccctgtgg caaactgacc aagcccaaac    840
ctcaagcaga atctaagaag aagaaaaagg aaggcaagaa acaggagaag atgctggatt    900
aaaagatgtc acctgtggaa cataaaaagg acatcagcaa acaggatcag ttaactattg    960
catttatatg taccgtaggc tttgtattca aaaattatct atagctaagt acacaataag   1020
caaaaacaa                                                           1029

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcccgagacg cctcccga                                                   18
```

What is claimed:

1. A pharmaceutical composition comprising protamine and an antisense oligonucleotide directed against nerve growth factor, where said composition is for intravesical administration to a subject.

2. The pharmaceutical composition of claim 1, where protamine comprises one or more of the following sequences:

MARYRCCRSQ SRSRYYRQRQ RSRRRRRRSC QTRRRAMRCC RPRYRPRCRR H (SEQ ID NO:1); MVRYRVRSLS ERSHEVYRQQ LHGQEQGHHG QEEQGLSPEH VEVYERTHGQ SHYRRRHCSR RRLHRIHRRQ HRSCRRRKRR SCRHRRRHRR GCRTRKRTCR RH (SEQ ID NO:2);

```
                                                (SEQ ID NO: 1)
MARYRCCRSQ SRSRYYRQRQ RSRRRRRRSC QTRRRAMRCC

RPRYRPRCRR H;

(SEQ ID NO: 2)
MVRYRVRSLS ERSHEVYRQQ LHGQEQGHHG QEEQGLSPEH

VEVYERTHGQ SHYRRRHCSR RRLHRIHRRQ HRSCRRRKRR

SCRHRRRHRR GCRTRKRTCR RH;

(SEQ ID NO: 3)
MRRQASLPAR RRRRVRRTRV VRRRRRVGRR RH;

(SEQ ID NO: 4)
PRRRRRSSSR PIRRRRRPRAS RRRRGGRRRR R;

(SEQ ID NO: 5)
PRRRRSSRRP VRRRRRPRVSR RRRRGGRRRR;

(SEQ ID NO: 6)
PRRRRSSSRP VRRRRRPRVSR RRRRGGRRRR;

(SEQ ID NO: 7)
PRRRRASRRI RRRRRPRVSR RRRRGGRRRR;
``` and/or
a peptide comprising the sequence RRRX$_1$ X$_2$ RRR where X$_1$ or X$_2$ or both is/are G or V or A (SEQ ID NO:8).

3. The pharmaceutical composition of claim 1 which is prepared by mixing together protamine and the antisense oligonucleotide directed against nerve growth factor shortly before administration to a subject.

4. A kit for preparing for intravesical administration to a subject, comprising protamine and an antisense oligonucleotide directed against nerve growth factor.

5. The pharmaceutical composition of claim 1, where the mass ratio of protamine to the antisense oligonucleotide directed against nerve growth factor is between about 5:1 to about 15:1 respectively.

6. The pharmaceutical composition of claim 1, where the mass ratio of protamine to the antisense oligonucleotide directed against nerve growth factor is about 10:1 respectively.

7. The pharmaceutical composition of claim 1, where the mass ratio of protamine to the antisense oligonucleotide directed against nerve growth factor is about 5:1 respectively.

8. The pharmaceutical composition of claim 1, comprising the antisense oligonucleotide directed against nerve growth factor in a concentration range between about 2 to about 20 µM.

9. The pharmaceutical composition of claim 1, comprising protamine in a concentration range between about 20 to about 200 µM.

10. The pharmaceutical composition of claim 1, comprising the antisense oligonucleotide directed against nerve growth factor in a concentration range between about 2 to about 20 µM and protamine in a concentration range between about 20 to about 200 µM.

11. The pharmaceutical composition of claim 1, where the antisense oligonucleotide is directed against nerve growth factor encoded by a mRNA having a corresponding cDNA sequence as follows:

```
                                            [SEQ ID NO: 9]
  1 tctgctttta ataagcttcc caatcagctc tcgagtgcaa agcgctctcc ctccctcgcc 61 cagccttcgt cctcctggcc cgctcctctc atccctccca ttctccattt cccttccgtt 121 ccctccctgt cagggcgtaa ttgagtcaaa ggcaggatca ggttccccgc cttccagtcc 181 aaaaatcccg ccaagagagc cccagagcag aggaaaatcc aaagtggaga gaggggaaga 241 aagagaccag tgagtcatcc gtccagaagg cggggagagc agcagcggcc caagcaggag 301 ctgcagcgag ccgggtacct ggactcagcg gtagcaacct cgccccctgc aacaaaggca 361 gactgagcgc cagagaggac gtttccaact caaaaatgca ggctcaacag taccagcagc 421 agcgtcgaaa atttgcagct gccttcttgg cattcatttt catactggca gctgtggata 481 ctgctgaagc agggaagaaa gagaaaccag aaaaaaaagt gaagaagtct gactgtggag 541 aatggcagtg gagtgtgtgt gtgcccacca gtggagactg tgggctgggc acacgggagg 601 gcactcggac tggagctgag tgcaagcaaa ccatgaagac ccagagatgt aagatcccct 661 gcaactggaa gaagcaattt ggcgcggagt gcaaatacca gttccaggcc tggggagaat 721 gtgacctgaa cacagccctg aagaccagaa ctggaagtct gaagcgagcc ctgcacaatg 781 ccgaatgcca gaagactgtc accatctcca agccctgtgg caaactgacc aagcccaaac 841 ctcaagcaga atctaagaag aagaaaaagg aaggcaagaa acaggagaag atgctggatt
```

-continued

```
 901 aaaagatgtc acctgtggaa cataaaaagg acatcagcaa acaggatcag ttaactattg 961 catttatatg taccgtaggc tttgtattca aaaattatct atagctaagt acacaataag 1021 caaaaacaa.
```

12. The pharmaceutical composition of claim 1, where the antisense oligonucleotide directed against nerve growth factor comprises the following sequence: GCCCGAGACGC-CTCCCGA (SEQ ID NO: 10).

* * * * *